(12) United States Patent
McMahon (10) Patent No.: US 6,994,723 B1
(45) Date of Patent: Feb. 7, 2006

(54) MEDICAL DEVICE MADE FROM SELF-STIFFENING COMPOSITE

(75) Inventor: James C. McMahon, Temecula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 243 days.

(21) Appl. No.: 10/442,796

(22) Filed: May 21, 2003

(51) Int. Cl.
*A61F 2/06* (2006.01)

(52) U.S. Cl. .................................. 623/1.49; 623/1.45

(58) Field of Classification Search ....... 623/1.39–1.48
See application file for complete search history.

(56) References Cited

U.S. PATENT DOCUMENTS

| | | | |
|---|---|---|---|
| 5,334,201 A | 8/1994 | Cowan | |
| 5,344,444 A | 9/1994 | Glastra | |
| 5,464,419 A | 11/1995 | Glastra | |
| 5,529,653 A | 6/1996 | Glastra | |
| 5,741,324 A | 4/1998 | Glastra | |
| 5,766,204 A | 6/1998 | Porter et al. | |
| 5,871,537 A | 2/1999 | Holman et al. | |
| 6,059,823 A | 5/2000 | Holman et al. | |
| 6,485,512 B1 | 11/2002 | Cheng | |
| 6,518,330 B2 * | 2/2003 | Moore et al. ............... | 523/200 |
| 2002/0111434 A1 | 8/2002 | White et al. | |
| 2002/0198342 A1 | 12/2002 | Kessler et al. | |

OTHER PUBLICATIONS

Kessler, M.R., et al., "Self-Activated Healing of Delamination Damage in Woven Composites," COMPOSITES: Part A 32 (2001) pp. 683-699.

White, S.R., et al., "Autonomic Healing of Polymer Composites," NATURE, vol. 409, Feb. 15, 2001, pp. 794-817.

Wool, Richard P., "A Material Fix," NATURE, vol. 409, Feb. 15, 2001, pp. 773-774.

Rule, Joseph D., et al., "ROMP Reactivity of endo- and exo-Dicyclopentadiene," MACROMOLECULES, Published on Web (Aug. 6, 2002).

Kessler, M.R., et al., "Cure Kinetics of the Ring-Opening Metathesis Polymerization of Dicyclopentadiene," Journal of Polymer Science, vol. 40, Apr. 16, 2002, pp. 2373-2383.

Brown, E.N., et al., "Fracture Testing of a Self-Healing Polymer Composite," Experimental Mechanics, vol. 42, No. 4, Dec. 2002, pp. 372-379.

* cited by examiner

*Primary Examiner*—David J. Isabella
*Assistant Examiner*—Hieu Phan
(74) *Attorney, Agent, or Firm*—Fulwider Patton LLP (57) ABSTRACT

Medical devices are made from a self-stiffening composite including a base material, a polymerizer and a corresponding activator for the polymerizer. The medical devices have an initial configuration in which the polymerizer and activator are separated from each other and an activated configuration in which the polymerizer and activator are brought into contact with each other. Polymerization is triggered when the polymerizer and activator are contacted together, forming a polymer that stiffens the medical device. The medical device may thus be flexible in the initial configuration so it can be easily advanced through tortuous passageways during delivery to a body lumen and further have sufficient radial strength in the activated configuration to hold open the body lumen after implantation.

26 Claims, 5 Drawing Sheets

MEDICAL DEVICE MADE FROM SELF-STIFFENING COMPOSITE

BACKGROUND OF THE INVENTION

This invention relates to medical devices, and more particularly implantable intraluminal devices for placement in a patient's body lumen, such as a blood vessel, to maintain the patency thereof. These devices are useful in the treatment of atherosclerotic stenosis in blood vessels.

Implantable intraluminal devices, such as stents, are generally tubular-shaped devices which function to hold open a segment of a blood vessel, coronary artery, or other anatomical lumen. They are particularly suitable for use to support and hold back a dissected arterial lining that can occlude the fluid passageway in the vessel. Similarly, vascular grafts may be implanted in vessels to strengthen or repair the vessel, or used in an anastomosis procedure to connect vessels segments together.

Stents often require extreme flexibility so as to be capable of being transported through varying and tortuous turns and diameters of the vessel pathway prior to arriving at the desired stenotic site. Expandable stents are so designed. Typically, expandable stents are delivered in a collapsed form to the stenotic region, expanded from within by a dilation balloon, and the ability to remain expanded so as to continue holding open the vessel after the balloon has been withdrawn.

Many expandable stents, however, do not retain a fully expanded state after the balloon has been withdrawn. Many such stents have been known to recoil after the inflation procedure due to elastic properties of the stent and applied stenotic pressure. If the recoil is great enough, the stent may also, due to lack of frictional resistance holding it in place, become dislodged from its location and migrate downstream. On such occasions, adequate lumenal flow can therefore be jeopardized. As a result, another procedure is needed to address a stent opening that has been so reduced. Therefore, it is important that a stent have sufficient radial strength to hold open and maintain the patency of a coronary artery.

Additionally, an expandable stent with plastic properties may be severely limited as to the degree of expandability of the stent from a deformed state into a permanently expanded configuration. It is therefore desirable for an expandable stent not to be so limited by its plastic properties and instead rely on different means for support when expanded beyond its ability to retain a plastically expanded shape.

There have been efforts to address the need to rigidize a stent after delivery and expansion. Some efforts have included, for example, the deposition of transformable materials in a stent wall. The mixing of epoxy components, for example, inside the wall of a stent has been heretofore disclosed. For example, it is known in the art that a stent may be constructed with a wall formed with breakable internal partitions separating mixable epoxy components. Such a stent may be designed to be delivered in a non-expanded state, and is thereafter subject to expansion by the dilation balloon. Accordingly, the expansion of the stent breaks open the partition walls allowing the epoxy components to mix, thereby hardening the resulting composition. Such stents, however, suffer the shortcoming that performance is dependent upon satisfactory formation and breaking of the partitions and the adequate intermixing of the epoxy components after the partitions have broken down. In addition, the prior art contains a stent with premixed epoxy enclosed in the stent wall. However, the art discloses that the pre-mixing stage takes place prior to insertion of the stent into the lumenal cavity and therefore requires the stent to not only be dispatched rapidly to the lumenal site, but also expanded before the mixed epoxy hardens.

What has been needed and heretofore unavailable is an improved stent or vascular graft that has a low profile and a high degree of flexibility so that it can be advanced through tortuous passageways and may be then expanded and more efficiently stiffened to hold open the body lumen into which it is expanded. The present invention satisfies this need.

SUMMARY OF THE INVENTION

Briefly, and in general terms, the present invention is directed to a medical device made from a self-stiffening composite that includes a base material, a polymerizer and a corresponding activator for the polymerizer. The polymerizer and the activator are dispersed in the base material, and the medical device has an initial configuration in which the polymerizer and activator are separated from each other and an activated configuration in which the polymerizer and activator are brought into contact with each other. Polymerization is triggered upon contact of the polymerizer and activator. After polymerization, the medical device may exhibit different properties than in the initial configuration. For instance, in the case of implantable intraluminal devices such as stents or vascular grafts, the device may be longitudinally and flexurally flexible in the initial configuration to facilitate delivery through tortuous body lumens while being stiffer in the activated configuration to provide sufficient radial strength to maintain the patency of a vessel and to resist collapse. In addition to stents and vascular grafts, the medical device of the present invention may take many forms, including, but not limited to, wound closures, embolic protection devices, graft attachment systems, anastomosis clips and other tube or wire implants.

As used herein, a polymerizer is a material that will form a polymer when it comes into contact with a corresponding activator for the polymerizer. Examples of polymerizers include monomers of polymers (such as styrene, ethylene, (meth)acrylates, and dicyclopentadiene), a monomer of a multimonomer polymer system (such as diols, diamines, and epoxide), and prepolymers (such as partially polymerized monomers still capable of further polymerization).

An activator, for example a catalyst or an initiator, triggers polymerization of the polymerizer upon contact with the polymerizer. A corresponding activator for a polymerizer is an activator that when brought into contact with that specific polymerizer will form a polymer. Examples of activators include ring opening metathesis polymerization (ROMP) catalysts and cyclic ester polymerization catalysts.

In one aspect of the present invention, the polymerizer is contained within microspheres when the medical device is in the initial configuration. When the medical device is deployed in the activated configuration, the microspheres in the base material rupture, releasing the polymerizer. The dispersion of the microspheres and activator in the base material provides a high degree of intermixing of the polymerizer and activator when the microspheres rupture, thus permitting the device to be efficiently stiffened to the desired amount of radial strength.

In another aspect of the present invention, an implantable intraluminal device formed of a self-stiffening composite and having a first delivery diameter is disposed on a balloon on a distal end portion of a delivery catheter, which is then advanced through the vasculature to a desired location. The balloon of the catheter is then inflated such that it expands the device. Once expanded to a second expanded diameter, the polymerizer contacts the activator and the device stiffens as polymerization takes place. Thereafter, the balloon is deflated and the catheter and balloon are withdrawn from the vasculature. The stiffened device remains implanted in the body lumen, providing sufficient radial strength to hold the lumen open.

A variety of manufacturing methods may be employed to manufacture medical devices having the self-stiffening composite of the present invention. In one method, the microspheres and the activator are dispersed in the base material without contacting the polymerizer and the activator to form a mixture. The medical device may then be formed from the mixture, such as by injection molding. In another method, the microspheres and activator are dispersed in a tubular body, such as a wire or fiber mesh tube, for example, by coating or immersing the tubular body in a mixture containing the microspheres and activator.

It is to be recognized that the medical device of the present invention can be self-expanding or balloon-expanded. Moreover, the self-stiffening composite of the present invention can be modified to be used in other body lumens, including highly tortuous and distal vasculature, as well as to create whole or portions of other medical devices.

Other features and advantages of the present invention will become more apparent from the following detailed description of the invention when taken in conjunction with the accompanying exemplary drawings.

DETAILED DESCRIPTION OF THE PREFERRED EMBODIMENTS

The present invention provides a medical device that is flexible in an initial configuration, yet is self-stiffening when placed in an activated configuration. The medical device of the present invention may take many forms, including, but not limited to, stents, vascular grafts, wound closures, embolic protection devices, graft attachment systems, anastomosis clips and other tube or wire implants. While a wide range of medical devices will benefit from the present invention, the invention as applied to implantable intraluminal devices, such as stents and vascular grafts, is described herein as only an example and is not meant to be limiting.

Figure 1:
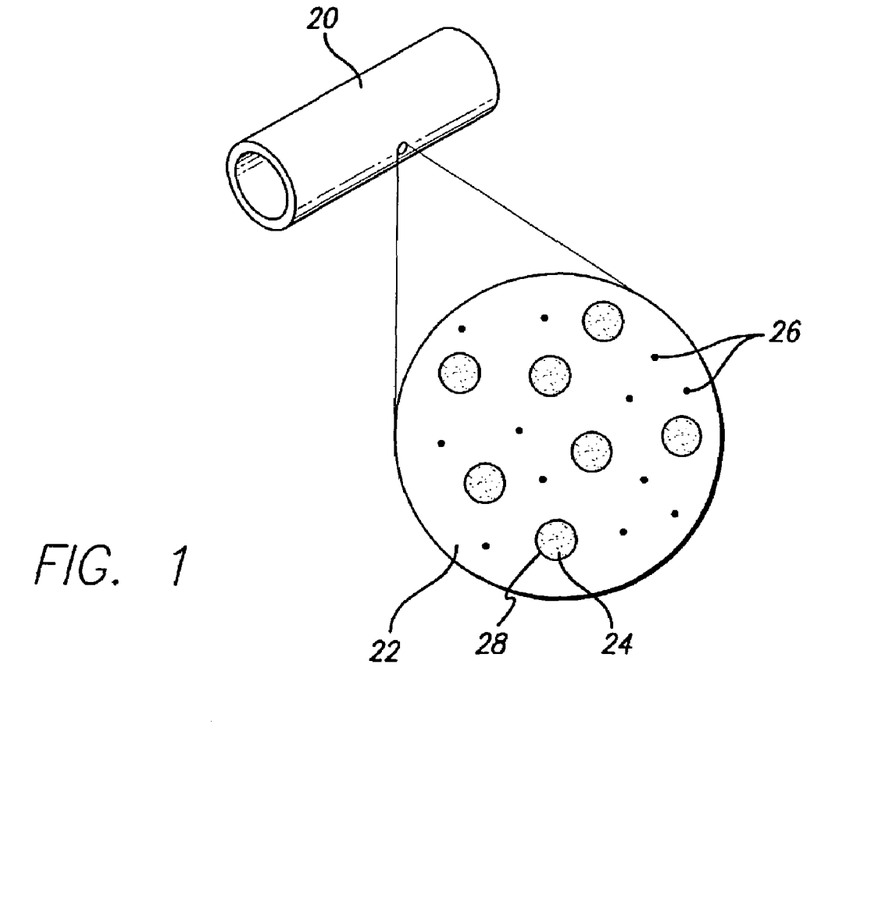
FIG. 1 is a schematic view of a stent in an initial configuration in accordance with the present invention, including a partially magnified, partially cut away view.

Referring now to the figures with more particularity, the present invention includes a medical device, and in particular a stent 20, having a tubular body formed of a base material 22, a polymerizer 24 and a corresponding activator 26 for the polymerizer 24. In an initial configuration, as shown in FIG. 1, the polymerizer 24 and activator 26 are separated from each other. As shown in FIG. 1, the polymerizer 24 may be contained within microspheres 28 that are dispersed in the base material 22. The microspheres 28 of the polymerizer 24 may be encapsulated, for example, in a urea formaldehyde shell to further isolate the polymerizer 24 from the activator 26. As is further shown in FIG. 1, the activator 26 may be provided in particle form dispersed in the base material 22. Further, the activator 26 may be encapsulated. In an alternative embodiment, the activator may be contained in microspheres while the polymerizer is not contained in microspheres.

Figure 2:
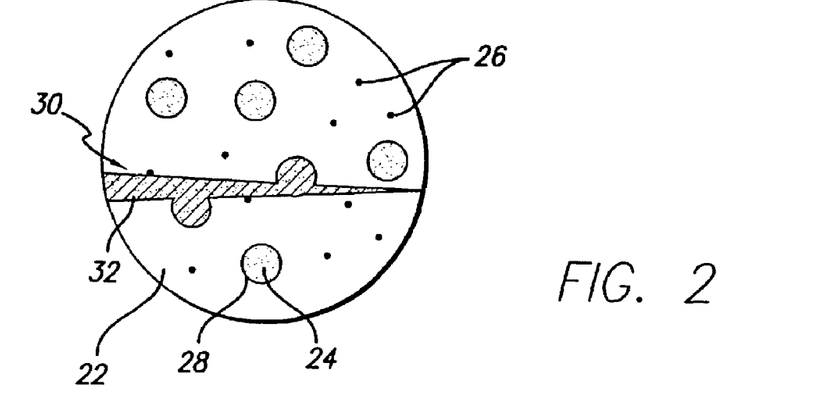
FIG. 2 is a magnified, cut away view of a portion of the stent of FIG. 1 in an activated configuration.

The stent 20 also has an activated configuration, shown in FIG. 2, in which the polymerizer 24 and activator 26 are brought into contact with each other. In the embodiment shown in FIG. 2, the stent 20 has been activated to rupture the microspheres 28, releasing the polymerizer 24 and causing contact with the activator 26. In FIG. 2, the stent 20 in the activated configuration has microcracks or open spaces 30 in the base material 22 that cause the microspheres 28 to rupture. The polymerizer 24 then wicks into the microcracks 30 by capillary action and contacts the activator 26. Contact between the polymerizer 24 and the activator 26 triggers polymerization of the polymerizer 22, forming a polymer 32. While only one microcrack 30 is depicted in FIG. 2, it is to be understood that any number of microcracks or open spaces may be formed in any pattern within the base material when the stent is in the activated configuration. In particular, a high degree of intermixing of the polymerizer and activator may be achieved in this embodiment. Depending on the dispersion of the polymerizer 24 and activator 26, as well as the configuration of the base material, the polymer 32 may form any desired pattern on the stent, such as a uniform layer over the entire stent or a series of cylindrical rings extending along the length of the stent.

Generally, the base material 22 is formed from a polymeric material that is bendable and flexible to enhance longitudinal and flexural flexibility of the stent 20 in its initial configuration. The base material may be selected from a wide variety of polymeric materials. For example, the base material may be selected from various polyurethanes, polyolefins, polyesters, polyamides, fluoropolymers and their copolymers, polyetherurethanes, polyesterurethanes, silicone, thermoplastic elastomer (e.g., C-FLEX), polyetheramide thermoplastic elastomer (e.g., PEBAX), fluoroelastomers, fluorosilicone elastomer, styrene-butadiene-styrene rubber, styrene-isoprene-styrene rubber, polyisoprene, neoprene (polychloroprene), polybutadiene, ethylene-propylene elastomer, chlorosulfonated polyethylene elastomer, butyl rubber, polysulfide elastomer, polyacrylate elastomer, nitrile rubber, isoprene (e.g., KRATON) and polyester thermoplastic elastomer (e.g., HYTREL). Other materials may also be added to the base material, such as fibers, fillers, adhesion modifiers, blowing agents, anti-oxidants, colorants, dyes and fragrances. Further, the base material may also be a shape memory polymer, be radiopacity enhanced and incorporate a material that generates a magnetic susceptibility artifact of the stent.

Additionally, a biodegradable base material may be employed in a self-stiffening composite of the present invention that contains sufficient polymerizer that, once polymerized in the activated configuration, possesses desired structure and smoothness without the need for further presence of the base material. Suitable biodegradable polymers may include L-polylactide, polylactic acid, polyglycolic acid, copolymers of lactic and glycolic acid, polycaprolactone, polyanhydrides, polyphosphoesters, polyphosphazenes, polyhydroxyvalerate and polyhydroxybutyrate.

The polymerizer 24 may include any suitable compound, such as a monomer or prepolymer, that polymerizes in the presence of a corresponding activator 26 to form a polymer 32 with the desired properties. In particular, the polymer 32 may be a stiffer material than the base material 22 so as to provide increased radial strength to the stent 20 when the stent is in the activated configuration. The corresponding activator 26 for the polymerizer 24 initiates the polymerization of the polymerizer 24 upon contact. The activator 26 may be a catalyst or an initiator.

The polymerizer 24 may include, for example, compounds such as cyclic olefins, including dicyclopentadiene, substituted dicyclopentadiene, norbornene, substituted norbornene, cyclooctadiene, and substituted cyclooctadiene. The corresponding activators 26 for these compounds are known ring opening metathesis polymerization (ROMP) catalysts such as Schrock catalysts and Grubbs catalysts, i.e. bis(tricyclohexylphosphine)benzylidine ruthenium(IV) dichloride.

Other suitable compounds for the polymerizer 24 include lactones, such as caprolacton, and lactams. The corresponding activators 26 for these compounds are cyclic ester polymerization catalysts and cyclic amide polymerization catalysts, such as scandium triflate.

The polymerizer 24 and/or activator 26 may optionally contain additional components, such as other monomers and/or prepolymers, stabilizers, solvents, viscosity modifiers such as polymers, odorants, colorants, dyes, blowing agents, antioxidants and co-catalysts. For example, the polymerizer 24 may include a cyclic olefin, as well as a co-catalyst, such as tungsten or molybdenum compounds, e.g. an organoammonium tungstate, an organoarsonium tungstate, an organophosphonium tungstate, an organoammonium molybdate, an organoarsonium molybdate or an organophosphonium molybdate. The corresponding activator 26 in this embodiment is the other co-catalyst, which may be an alkyl aluminum compound (such as an alkoxyalkylaluminum halide, an aryloxyalkylaluminum halide or a metaloxyalkylaluminum halide in which the metal in the compound is tin, lead or aluminum), or may be an organic tin compound (such as a tetraalkyltin, a trialkyltin hydride or a triaryltin hydride).

In another example, the polymerizer 24 may include unsaturated compounds such as acrylates, acrylic acids, alkyl acrylates, alkyl acrylic acids, styrenes, isoprene or butadiene as well as a co-catalyst, such as either an organohalide (such as 1-chloro-1-phenylethane) or a copper(I) source (such as copper(I) bipyridyl complex). The co-catalyst not included in the polymerizer 24 would be used as the corresponding activator 24. Alternatively, the co-catalysts could be a peroxide (such as benzoyl peroxide) and a nitroxo precursor (such as 2,2,6,6-tetramethylpiperidinyl-1-oxy (TEMPO)), one of which would be included in the polymerizer 24 and one of which would be used as the corresponding activator 24.

In yet another example, the polymerizer 24 may include isocyanate functional groups with hydroxyl functional groups either contained in a single compound or in two different compounds. In this embodiment, the polymerizer 24 may contain a blowing agent, such as a volatile liquid like dichloromethane. A co-catalyst, such as an alkyltin compound (such as stannous 2-ethylhexanoate) or a tertiary amine (such as diazabicyclo(2,2,2)octane (DABCO)), may also be included in the polymerizer 24.

Figure 3:
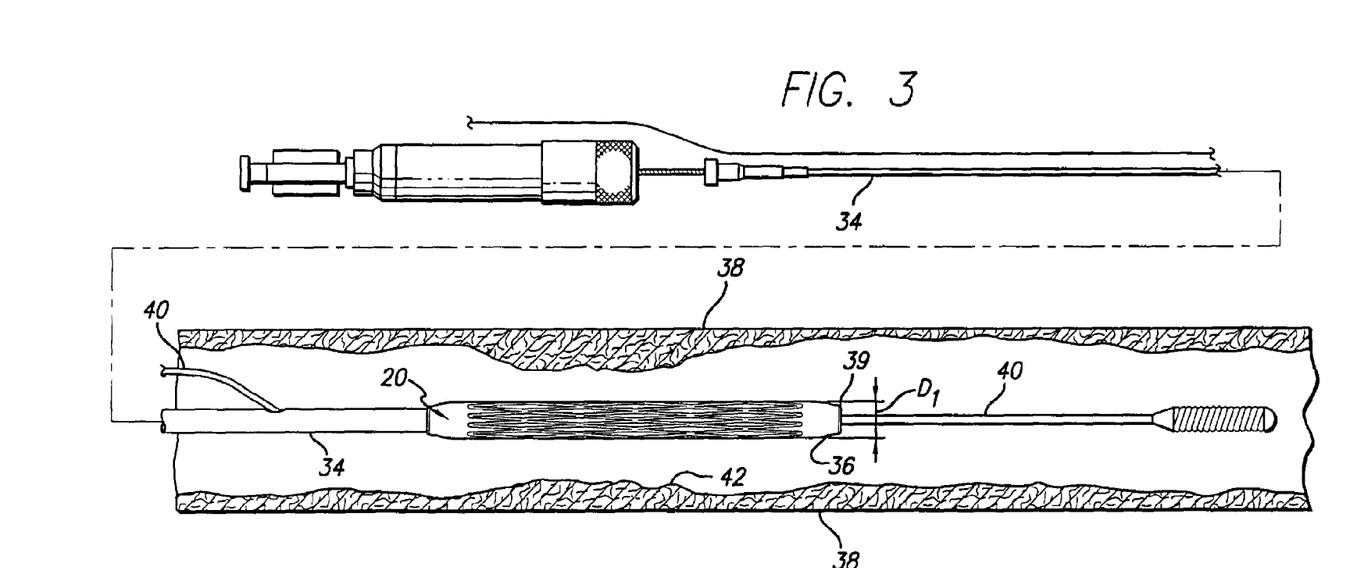
FIG. 3 is a side plan view, partially in section, of a stent embodying features of the invention mounted on a delivery catheter and disposed within an artery.
Figure 6:
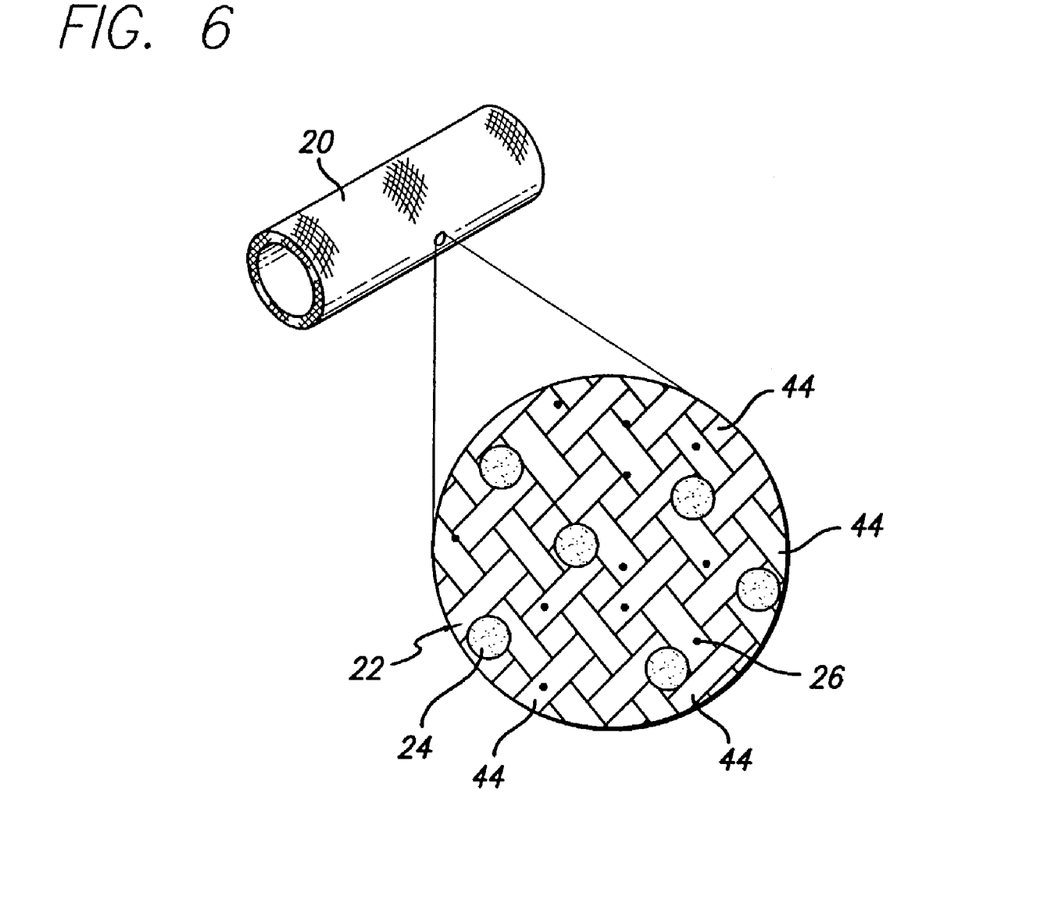
FIG. 6 is a schematic view of a mesh stent in an initial configuration, including a partially magnified, partially cut away view according to one embodiment of the present invention.

Referring now to FIG. 3, the stent 20 in its initial configuration may be mounted onto a delivery catheter 34. In this embodiment, the stent 20 includes the base material 22, polymerizer 24 and activator 26. One useful stent design may be a woven or knitted mesh (FIG. 6). In its initial configuration, the stent 20 has a first delivery diameter $D_1$, wherein the polymerizer and activator separated, as shown in FIG. 1. The delivery catheter 34 has an expandable portion or balloon 36 for expanding the stent 20 within an artery 38. The artery 38, as shown in FIG. 3, has an occluded portion of the arterial passageway that has been opened by a previous procedure, such as angioplasty.

The delivery catheter 34 onto which the stent 20 is mounted is essentially the same as a conventional balloon dilatation catheter for angioplasty procedures or other stent delivery system. The balloon 36 may be formed of suitable materials such as polyethylene, polyethylene terephthalate, polyvinyl chloride, nylon and ionomers such as SURLYN manufactured by the Polymer Products Division of the Du Pont Company. Other polymers may also be used. In order for the stent 20 to remain in place on the balloon 36 during delivery to the site of the damage within the artery 38, the stent 20 may be crimped or radially compressed onto the balloon in a known manner (FIG. 3).

While the stent 20 generally has a tubular body in its initial configuration, the stent may be expanded to varying degrees along its length, and therefore can have a tapered configuration after expansion. Similarly, the balloon 36 may be provided with an inflated shape other than cylindrical, e.g., tapered, to facilitate implantation of the tapered stent in a variety of body lumen shapes.

Figure 4:
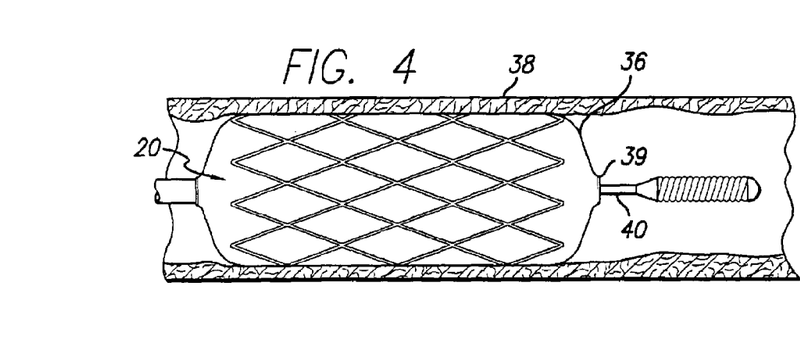
FIG. 4 is a side plan view, partially in section, similar to that shown in FIG. 3, wherein the stent is expanded within an artery.

In one embodiment, the delivery of the stent 20 is accomplished in the following manner. The stent 20 is first disposed onto the inflatable balloon 36 on the distal end portion 39 of the delivery catheter 34 by crimping or compressing the stent in a known manner. The catheter-stent assembly is introduced within the patient's vasculature (e.g., an artery or vein) in a conventional Seldinger technique through a guiding catheter (not shown). A guide wire 40 is disposed across the damaged arterial section and then the catheter-stent assembly is advanced over a guide wire 40 within the artery 38 until the stent 20 is positioned at a desired location or target site 42. The balloon of the catheter is inflated, expanding the stent and forcing the stent against the artery 38, which is illustrated in FIG. 4. During expansion, the diameter of the stent 20 increases from the first delivery diameter $D_1$ to a second expanded diameter $D_2$. While not shown in the drawing, the artery is preferably expanded slightly by the expansion of the stent to seat or otherwise fix the stent to prevent migration of the stent. In some circumstances during the treatment of stenotic portions of an artery, the artery may have to be expanded considerably in order to facilitate passage of blood or other fluid therethrough. The stent 20 may also be self-expanding in some embodiments, wherein the base material 22 embodies shape memory characteristics.

Figure 5:
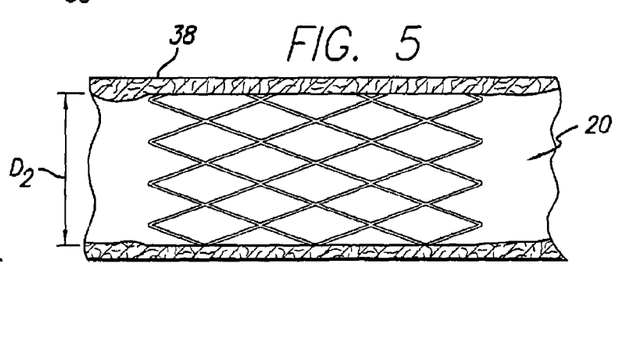
FIG. 5 is a side plan view, partially in section, depicting the expanded stent of FIG. 4 within the artery after withdrawal of the delivery catheter.

Expanded to the second expanded diameter $D_2$, the stent 20 serves to hold open the artery 38 after the balloon is deflated and the catheter 34 is withdrawn, as illustrated by FIG. 5. In this form the stent 20 is in its activated configuration, wherein the polymerizer 24 and the activator 26 been brought into contact, as shown in FIG. 2. Thus, the stent 20 is self-stiffening in the activated configuration. The expansion of the stent 20 causes the base material 22 to undergo physical deformation resulting in microcracks, voids or other interstitial spaces and rupturing the microspheres so as to release the polymerizer for polymerization. Although the stent 20 may be flexible in the initial configuration, the stent 20 stiffens after polymerization in the activated configuration. Thus, in the activated configuration, the stent 20 provides the necessary radial stiffness to support the wall of the artery 38 to permit blood flow through the vessel or to tack up and hold in place small flaps or dissections in the wall of the artery 38.

The stent 20 according to the present invention may be constructed in a variety of ways. As is generally illustrated in FIGS. 1 and 2, the stent 20 may be made of a composite material wherein the microspheres 28 and activator 26 are dispersed in the base material. The microspheres 28 may be encapsulated according to standard microencapsulation techniques known in the art. For example, the polymerizer 24 may be contained within microspheres 28 that are encapsulated in a shell made from urea-formaldehyde formed by in situ polymerization, gelatin formed by complex coacervation, polyurea formed by the reaction of isocyanates with a diamine or a triamine or a polyamide formed by the use of a suitable acid chloride and a water soluble triamine. The activator 26 may optionally be coated onto the encapsulating shell.

In one method of constructing the stent 20, the base material 22 is a polymer that is formed around the microspheres 28 and activator 26. For example, a monomer of the base material 22 may be mixed with the microspheres 28 and activator 26 and polymerized to form the composite material. The activator 26 may be chosen to be a catalyst for the polymerization of the base material 22 and a catalyst for the polymerizer 24, such as when the monomer of the base material 22 and the polymerizer 24 are both dicyclopentadiene and the catalyst is Grubbs catalyst. Similarly, the monomer of the base material 22 and the polymerizer 24 may both be caprolactone and the catalyst may be scandium triflate.

In another method, the base material 22 is polymerized prior to incorporating the microspheres 28 and activator 26. For example, the base material 22 may be dissolved in a solvent into which the microspheres 28 and activator 26 are then mixed. The solvent is then removed, leaving the composite material.

With either method, the composite material may then be formed into a tubular body, such as by injection molding, to form the stent 20. Alternatively, the composite material may be formed into a flat sheet which is rolled into a tubular body and longitudinally bonded to form the stent 20. Other suitable methods of forming the tubular body of the stent 20 may also be used.

In another embodiment, the medical device may be a vascular graft or stent 20 (FIG. 6) formed of a mesh of woven or knitted fibers 44 of the base material 22. The fibers 44 may be monofilament, multifilament, staple yarn or a combination thereof and may be formed from any suitable polymeric material, particularly polyamides such as nylons, polyesters such as polyethylene terephthalate (DACRON) and polytetrafluoroethylene (PTFE). In this embodiment, the polymerizer 24 and activator 26 are dispersed in the base material 22. The polymerizer 24 may be embedded in the mesh such that when the stent 20 is expanded into the activated configuration, movement of the fibers 44 causes the microspheres 28 to rupture, thereby releasing the polymerizer 24. For example, the microspheres 28 may be generally embedded in interstitial spaces 46 located between the fibers 44. When the stent 20 is expanded, the fibers 44 shift, altering the interstitial spaces 46 and rupturing the embedded microspheres 28. Further, the force exerted on the stent 20 from the expansion of the balloon can cause the microspheres to rupture.

The microspheres 28 and activator 26 may be loaded or dispersed into the woven fibers 44 by a number of different methods known to those skilled in the art. For example, the microspheres 28 and activator 26 may be mixed into a solvent and the woven tubular body then immersed in the solvent. Individual fibers 44 may also be soaked or coated with the solvent and then woven into the tubular body. When the solvent is removed, the microspheres 28 and activator 26 are left dispersed among the fibers 44. The microspheres 28 and activator 26 may also be mixed into a liquid polymeric material that is deposited onto the woven tubular structure by similar methods or by dip coating, spray coating, brushing or thermal spraying.

Figure 7A:
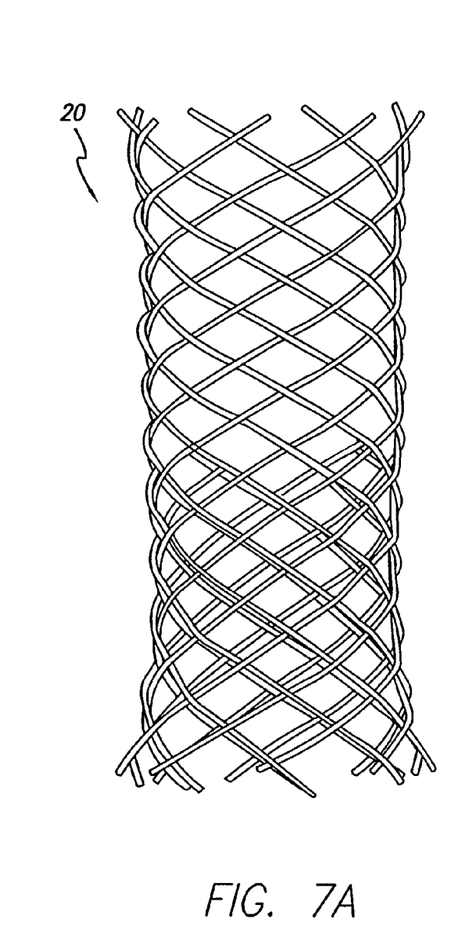
FIGS. 7A and 7B depict perspective views of alternate stent designs suitable for use with the present invention.
Figure 7B:
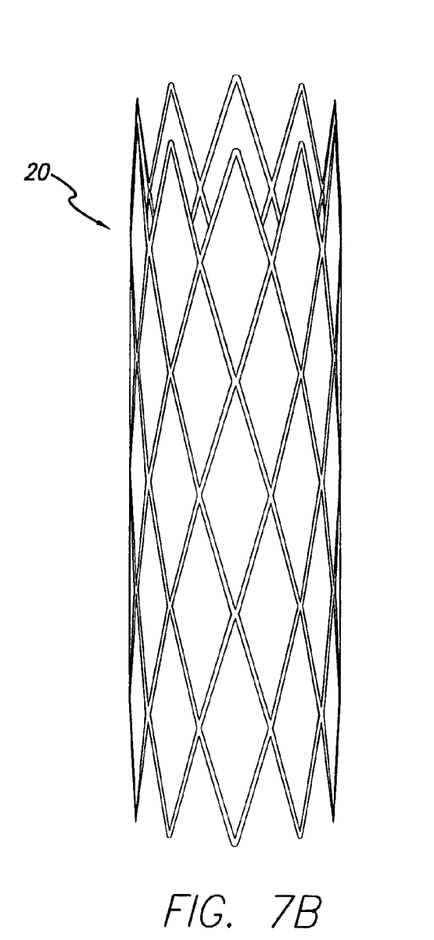

In addition to the polymeric mesh stent of FIG. 6, other stent designs may benefit from a similar loading of the polymerizer and/or activator into interstitial spaces. For example, stent 20 may be formed of flexible woven wire (FIG. 7A) or wire mesh (FIG. 7B). The wire in FIGS. 7A and 7B may be formed from a variety of metals including stainless steel, titanium, tungsten, tantalum, vanadium, gold (and its alloys), silver (and its alloys), palladium, platinum and iridium. Further, the wire may be formed from certain biocompatible metal alloys including (1) iron-carbon alloys, e.g., ASTM F138, ASTM F139, AISI 316L (18Cr-14Ni-2.5Mb); (2) cobalt-chromium alloys, e.g., ASTM F90 (Co-20Cr-20W-10Ni) [available as trade name products HAYNES 25 and L-605 (Carpenter)], ASTM F562 (35Co-35Ni-20Cr-10Mo) [available as trade name product MP35N], ASTM F1058 (40Co-20Cr-16Fe-15Ni-7Mo) [available as trade name product ELGILOY (Elgin)], HAYNES Alloy 188 (Co-24Ni-23Cr-15W); and (3) nickel-titanium alloys, e.g., nitinol, F 2063. The stent designs of FIGS. 7A and 7B typically provide the desired flexibility for delivery, but may not provide the necessary radial strength to support the body lumen once the stent is implanted. By incorporating the polymerizer and activator into these stent designs, greater radial strength may be provided for implantation without compromising the desired flexibility during delivery. Other such stent designs may benefit from the self-stiffening composite of the present invention.

The stent 20 may optionally include a thin film of polymer surrounding the stent 20 on at least one side to prevent the polymerizer from diffusing into the body lumen after the polymerizer is released from the microspheres and before polymerization is complete. The thin film of polymer may be applied to the stent 20 by any suitable means such as spray coating, dip coating, brushing or heat fusion lamination.

The properties of the stent 10 may vary by alteration of the type of polymerizer 24 and base material 22. These materials are chosen to fill particular mechanical requirements for the stent, such as flexibility in the initial configuration and radial stiffness and strength in the activated configuration. Further, the amount of polymerizer and activator added to the stent as well as the pattern of dispersion of the polymerizer and activator within the stent may also vary according to design requirements such as flexibility and radial stiffness.

Figure 8:
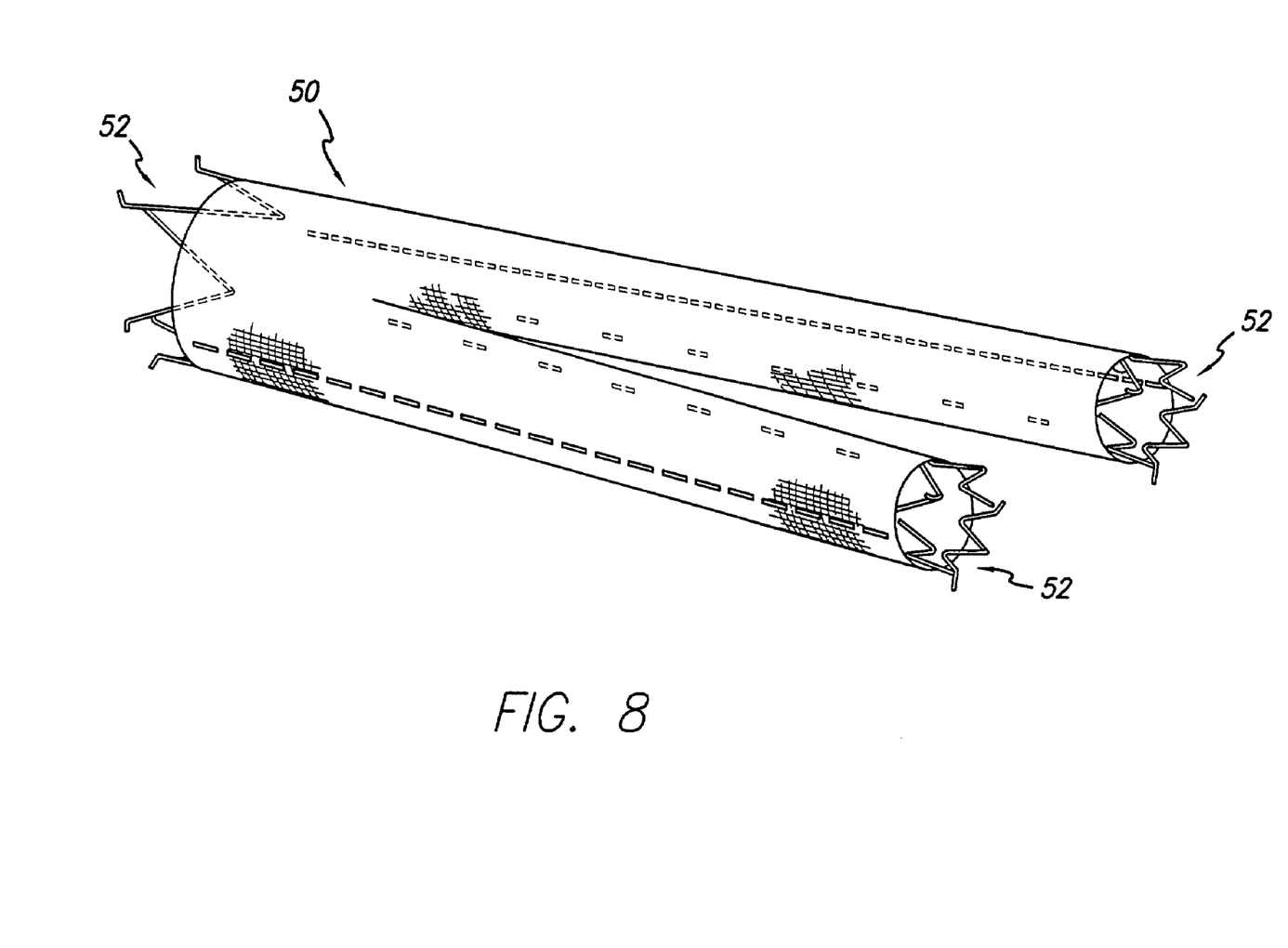
FIG. 8 is a perspective view of a bifurcated graft suitable for use with the present invention.

While the foregoing embodiments have been described with respect to a stent, they may also be adapted for use in a vascular graft. The graft may have a tubular body in its initial configuration, similar to the stents described in the foregoing embodiments. The present invention may also be applied to a bifurcated graft 50, as shown in FIG. 8, in a similar manner. As heretofore described regarding stents, the grafts may be constructed with a polymerizer and activator in accordance with the present invention. These grafts may be of various designs, including each of the embodiments described with respect to stents. In many grafts, such as those used for repairing an abdominal aortic aneurysm, an attachment system 52 (FIG. 8) is positioned proximate each opening of the graft. Such attachment systems 52 are well known in the art and the stents of the foregoing embodiments may be easily modified to include the attachment systems for use as a graft.

While particular forms of the invention have been illustrated and described with regard to certain medical devices, it will also be apparent to those skilled in the art that various modifications can be made without departing from the scope of the invention. More specifically, it should be clear that the present invention is not limited to stents and vascular grafts. Likewise, the invention is not limited to any particular method of forming the underlying medical device structure. While certain aspects of the invention have been illustrated and described herein in terms of its use as a stent, it will be apparent to those skilled in the art that the stent can be used in other body lumens. Further, the particular materials used, the particular stent designs and the like that have been described herein are provided as examples only. Other modifications and improvements may be made without departing from the scope of the invention. Accordingly, it is not intended that the invention be limited, except as by the appended claims.

What is claimed is:

1. An expandable medical device having a delivery configuration and an expanded configuration, comprising:
   a tubular body formed from the base material;
   a polymerizer; and
   a corresponding activator for the polymerizer, wherein the polymerizer and activator are dispersed in the base material, and wherein the medical device has an initial delivery configuration in which the polymerizer and activator are separated from each other and an expanded configuration in which the polymerizer and activator are brought into contact with each other.

2. The medical device of claim 1, wherein the polymerizer is contained within microspheres when the medical device is in the initial configuration.

3. The medical device of claim 2, wherein the medical device is configured to rupture the microspheres so as to release the polymerizer when the medical device is deployed in the activated configuration.

4. The medical device of claim 1, wherein the base material is a polymer.

5. The medical device of claim 1, wherein the polymerizer includes a monomer selected from the group consisting of cyclic olefins, lactones, lactams, acrylates, acrylic acids, alkyl acrylates, alkyl acrylic acids, styrenes, isoprene and butadiene.

6. The medical device of claim 5, wherein the corresponding activator for the polymerizer is selected from the group consisting of ROMP catalysts and cyclic ester polymerization catalysts.

7. The medical device of claim 1, wherein the base material embodies shape memory characteristics.

8. The medical device of claim 1, wherein the medical device is implantable in a human body.

9. The medical device of claim 8, wherein the implantable medical device is configured as a stent.

10. The medical device of claim 8, wherein the implantable medical device is configured as a vascular graft.

11. An expandable implantable intraluminal device, comprising:
   a tubular body formed of a base material, a polymerizer contained within microspheres and a corresponding activator for the polymerizer, wherein the microspheres and activator are dispersed in the base material, the tubular body having a first delivery diameter in which the polymerizer and activator are separated from each other and a second expanded diameter in which the polymerizer and activator are brought into contact with each other.

12. The implantable intraluminal device of claim 11, wherein the tubular body is configured to rupture the microspheres so as to release the polymerizer when the implantable intraluminal device is deployed in the second expanded diameter.

13. A method for manufacturing an expandable medical device, comprising:
   providing a tubular body formed from the base material;
   dispersing a polymerizer and a corresponding activator for the polymerizer into the base material without contacting the polymerizer and the activator so as to form a mixture; and
   forming an expandable medical device from the mixture wherein expansion causes said polymerizer and activator to contact one another.

14. The method of claim 13, further comprising incorporating the polymerizer into microspheres prior to dispersing the polymerizer into the base material.

15. The method of claim 13, wherein forming the medical device includes injection molding the mixture to form a tubular body.

16. The method of claim 15, wherein forming the medical device includes configuring an implantable device suitable for use in a human body.

17. The method of claim 16, wherein configuring the implantable device includes configuring a stent.

18. The method of claim 16, wherein configuring the implantable medical device includes configuring a vascular graft.

19. A method for manufacturing a medical device, comprising:
   providing a tubular body formed from the base material;
   forming a tubular body from the base material; and
   dispersing a polymerizer and a corresponding activator for the polymerizer into the base material of the tubular body without contacting the polymerizer and the activator.

20. The method of claim 19, wherein dispersing the polymerizer and the activator into the base material of the tubular body includes immersing the tubular body in a mixture containing the polymerizer and the activator.

21. The method of claim 19, further comprising incorporating the polymerizer into microspheres prior to dispersing the polymerizer into the base material of the tubular body.

22. The method of claim 19, wherein forming the tubular body includes configuring a stent.

23. The method of claim 19, wherein forming the tubular body includes configuring a vascular graft.

24. A method of delivering an implantable intraluminal device to a desired location within a patient's vasculature, the method comprising:
   providing a delivery catheter having a distal end portion, a balloon formed on the distal end portion of the catheter, and an implantable intraluminal device disposed on the balloon and configured from a base material, a polymerizer, and a corresponding activator for the polymerizer, wherein the polymerizer and activator are dispersed in the base material;

advancing the distal end portion of the catheter, the balloon and the implantable intraluminal device though the vasculature to a desired location;

inflating the balloon so as to expand the implantable intraluminal device at the desired location and to contact the polymerizer with the activator;

deflating the balloon; and withdrawing the catheter and the balloon from the vasculature.

25. The method of claim 24, wherein inflating the balloon so as to contact the polymerizer with the activator triggers polymerization of the polymerizer.

26. The method of claim 25, wherein deflating the balloon is performed after polymerization of the polymerizer is completed.

* * * * *